United States Patent [19]
Bartley

[11] Patent Number: 5,687,744
[45] Date of Patent: Nov. 18, 1997

[54] HAND SUPPORT FOR CONTROLLING SCAR TISSUE

[76] Inventor: Barbara L. Bartley, 749 Scotland Rd. Apt. 6C, Orange, N.J. 07050

[21] Appl. No.: 751,750
[22] Filed: Nov. 18, 1996
[51] Int. Cl.[6] .................................................. A61F 5/37
[52] U.S. Cl. ........................... 128/878; 128/879; 2/20
[58] Field of Search .............................. 128/846, 877, 128/878, 879, 880; 602/20–22; 273/84 R; 482/108, 109; 2/16, 20, 21

[56] References Cited

U.S. PATENT DOCUMENTS

| | | | |
|---|---|---|---|
| 1,200,580 | 10/1916 | Brenner | 2/20 |
| 1,708,757 | 4/1929 | Freileweh | 602/20 |
| 2,546,118 | 3/1951 | Wright | 128/879 |
| 3,736,926 | 6/1973 | Irby | 128/879 |
| 4,558,694 | 12/1985 | Barber | 602/21 |

*Primary Examiner*—Michael A. Brown

[57] ABSTRACT

A hand support for controlling scar tissue including a planar member comprised of a flexible material. The planar member has a plurality of digit apertures therethrough. The planar member is dimensioned to be worn on a hand of a user.

5 Claims, 3 Drawing Sheets

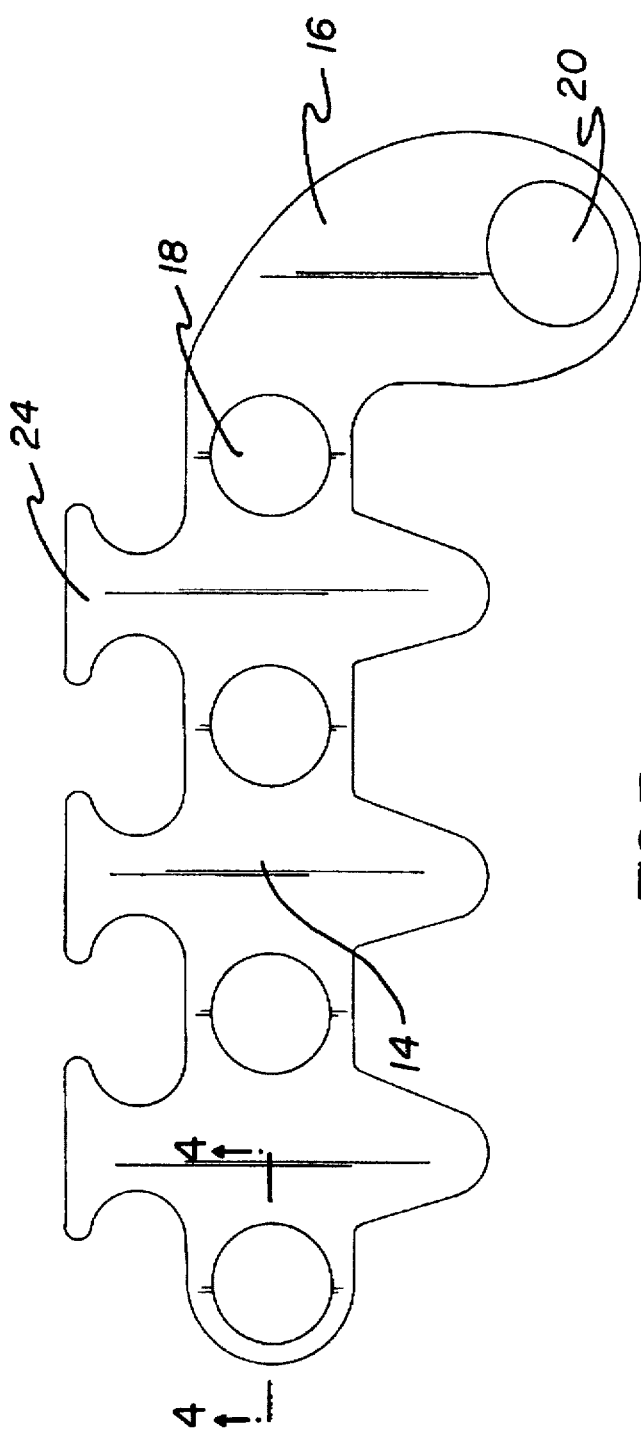
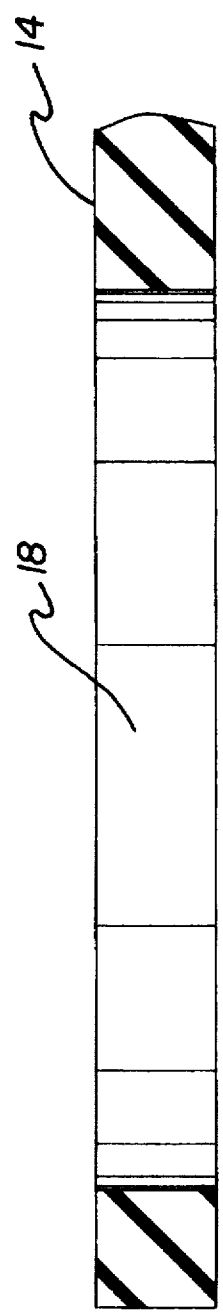
FIG. 3
FIG. 4

HAND SUPPORT FOR CONTROLLING SCAR TISSUE

BACKGROUND OF THE INVENTION

1. Field of the Invention

The present invention relates to a hand support for controlling scar tissue and more particularly pertains to applying pressure to an individual's hand to preclude excessive scar tissue buildup during healing with a hand support for controlling scar tissue.

2. Description of the Prior Art

The use of first aid gloves is known in the prior art. More specifically, first aid gloves heretofore devised and utilized for the purpose of protecting hands of a wearer are known to consist basically of familiar, expected and obvious structural configurations, notwithstanding the myriad of designs encompassed by the crowded prior art which have been developed for the fulfillment of countless objectives and requirements.

By way of example, U.S. Pat. No. 5,328,449 to Andrews et al. discloses a wound dressing for the hands.

U.S. Pat. No. 4,272,849 to Thurston et al. discloses a flexible form fitting glove.

U.S. Pat. No. Des. 335,368 to Houston discloses the ornamental design for a support glove.

U.S. Pat. No. 4,360,972 to Montgomery discloses a method of selecting one of a plurality of standard size burn gloves.

U.S. Pat. No. 5,156,168 to Canterna discloses a support for arthroscopy.

While these devices fulfill their respective, particular objective and requirements, the aforementioned patents do not describe a hand support for controlling scar tissue for applying pressure to an individual's hand to preclude excessive scar tissue buildup during healing.

In this respect, the hand support for controlling scar tissue according to the present invention substantially departs from the conventional concepts and designs of the prior art, and in doing so provides an apparatus primarily developed for the purpose of applying pressure to an individual's hand to preclude excessive scar tissue buildup during healing.

Therefore, it can be appreciated that there exists a continuing need for new and improved hand support for controlling scar tissue which can be used for applying pressure to an individual's hand to preclude excessive scar tissue buildup during healing. In this regard, the present invention substantially fulfills this need.

SUMMARY OF THE INVENTION

In the view of the foregoing disadvantages inherent in the known types of first aid gloves now present in the prior art, the present invention provides an improved hand support for controlling scar tissue. As such, the general purpose of the present invention, which will be described subsequently in greater detail, is to provide a new and improved hand support for controlling scar tissue and method which has all the advantages of the prior art and none of the disadvantages.

To attain this, the present invention essentially comprises a planar member comprised of a flexible material having a generally J-shaped main portion. The main portion has an elongated upper portion and a generally arcuate lower portion. The elongated upper portion has four spaced apart digit apertures therethrough. The lower portion has a single digit aperture therethrough. The single digit aperture of the lower portion has a diameter greater than a diameter of the four digit apertures of the elongated upper portion.

The planar member is dimensioned to be worn on a hand of a user. The device includes three generally T-shaped members each having lower ends integral with a first edge of the elongated upper portion of the planar member. The device includes three arcuate members each having lower ends integral with a second edge of the elongated upper portion of the planar member.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved hand support for controlling scar tissue which has all the advantages of the prior art first aid gloves and none of the disadvantages.

It is another object of the present invention to provide a new and improved hand support for controlling scar tissue which may be easily and efficiently manufactured and marketed.

It is a further object of the present invention to provide a new and improved hand support for controlling scar tissue which is of durable and reliable construction.

An even further object of the present invention is to provide a new and improved hand support for controlling scar tissue which is susceptible of a low cost of manufacture with regard to both materials and labor, and which accordingly is then susceptible of low prices of sale to the consuming public, thereby making such a hand support for controlling scar tissue economically available to the buying public.

Still yet another object of the present invention is to provide a new and improved hand support for controlling scar tissue which provides in the apparatuses and methods of the prior art some of the advantages thereof, while simultaneously overcoming some of the disadvantages normally associated therewith.

Even still another object of the present invention is to provide a new and improved hand support for controlling scar tissue and more particularly pertains to applying pressure to an individual's hand to preclude excessive scar tissue buildup during healing with a hand support for controlling scar tissue.

Lastly, it is an object of the present invention to provide a new and improved hand support for controlling scar tissue including a planar member comprised of a flexible material. The planar member has a plurality of digit apertures therethrough. The planar member is dimensioned to be worn on a hand of a user.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a plan view of the preferred embodiment of the present invention.

FIG. 4 is a cross-sectional view as taken along line 4—4 of FIG. 3.

The same reference numerals refer to the same parts through the various Figures.

DESCRIPTION OF THE PREFERRED EMBODIMENT

Figures 1, 2:
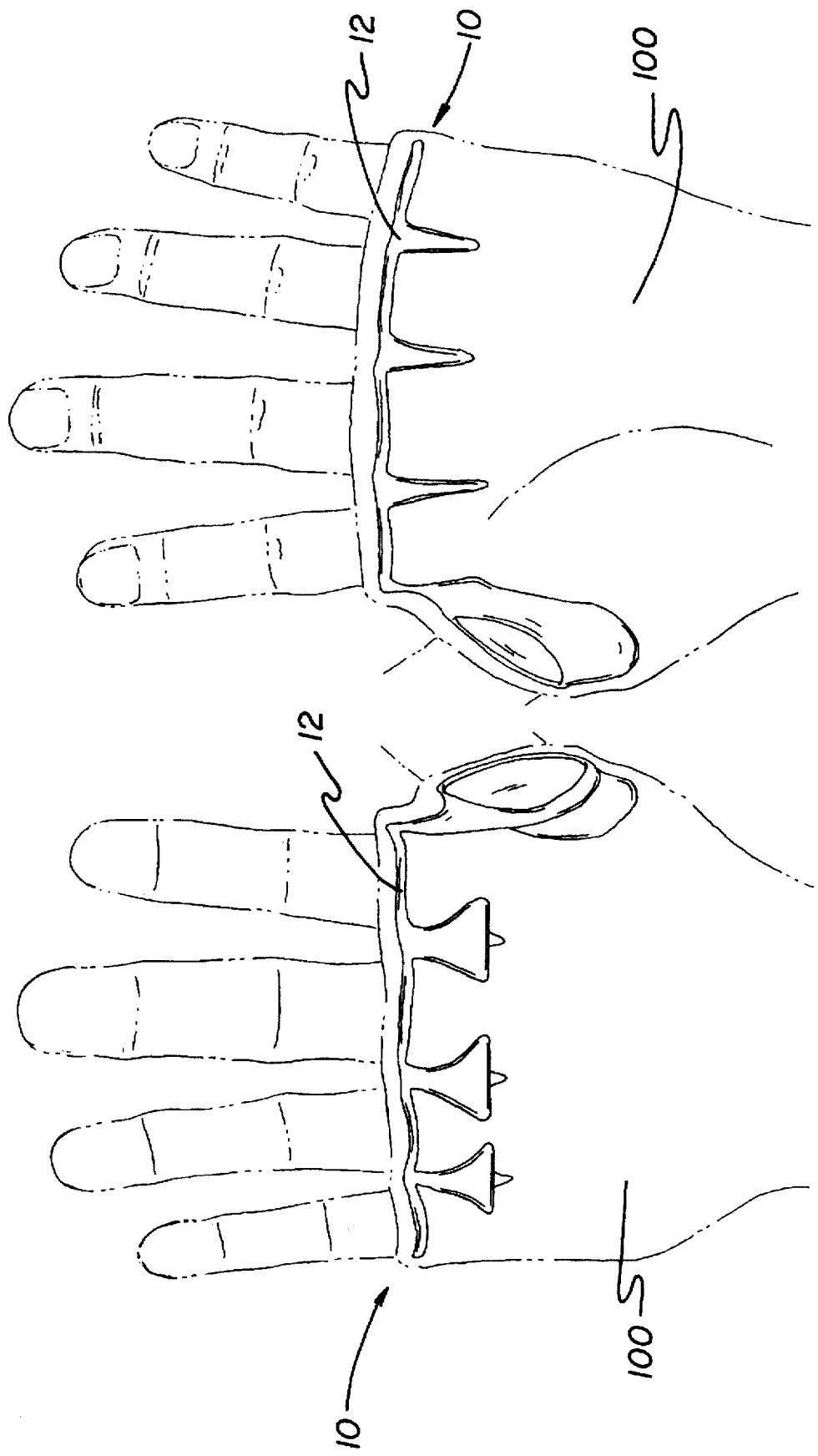
FIG. 1 is a perspective view of the preferred embodiment of the hand support for controlling scar tissue constructed in accordance with the principles of the present invention.
FIG. 2 is a rear view of the present invention in place on a user's hand.

With reference now to the drawings, and in particular, to FIGS. 1-4 thereof, the preferred embodiment of the new and improved hand support for controlling scar tissue embodying the principles and concepts of the present invention and generally designated by the reference number 10 will be described.

Specifically, it will be noted in the various Figures that the device relates to a new and improved hand support for controlling scar tissue for applying pressure to an individual's hand to preclude excessive scar tissue buildup during healing. In its broadest context, the device consists of a planar member, three generally T-shaped members, and three arcuate members. Such components are individually configured and correlated with respect to each other so as to attain the desired objective.

The device 10 includes a planar member comprised of a flexible material having a generally J-shaped main portion 12. The main portion 12 has an elongated upper portion 14 and a generally arcuate lower portion 16. The elongated upper portion 14 has four spaced apart digit apertures 18 therethrough. The four spaced apart digit apertures 18 are dimensioned to receive four fingers of a user's hand 100 therethrough. The lower portion 16 has a single digit aperture 20 therethrough. The single digit aperture 20 of the lower portion 16 has a diameter greater than a diameter of the four digit apertures 18 of the elongated upper portion 14. The single digit aperture 20 is dimensioned to receive the thumb of the user's hand 100 therethrough. The planar member 12 is dimensioned to be worn on a hand 100 of a user. The planar member 12 can have a crease extending through the four spaced apart digit apertures 18 and the single digit aperture 20 to allow the planar member 12 to be properly extended over the webs between the fingers of the user thereby providing direct pressure over the web spaces of the hand 100 to help control scar tissue formation or reduce edema. Placement of the planar member 12 between fingers will aid in the stretching of tight collateral ligaments of the MCP joints.

The device 10 also includes three generally T-shaped members 24 each having lower ends integral with a first edge of the elongated upper portion 14 of the planar member 12. Once the planar member 12 is in place between the finger's of the hand 100 of the user, the T-shaped members 24 are folded into the palm area of the hand 100.

Lastly, the device 10 includes three arcuate members 28 each having lower ends integral with a second edge of the elongated upper portion 14 of the planar member 12. Once the planar member 12 is in place between the finger's of the hand 100 of the user, the arcuate members 28 are folded back over the top of the hand 100 to prevent the planar member 12 from slipping off of the hand 100.

Figure 5:
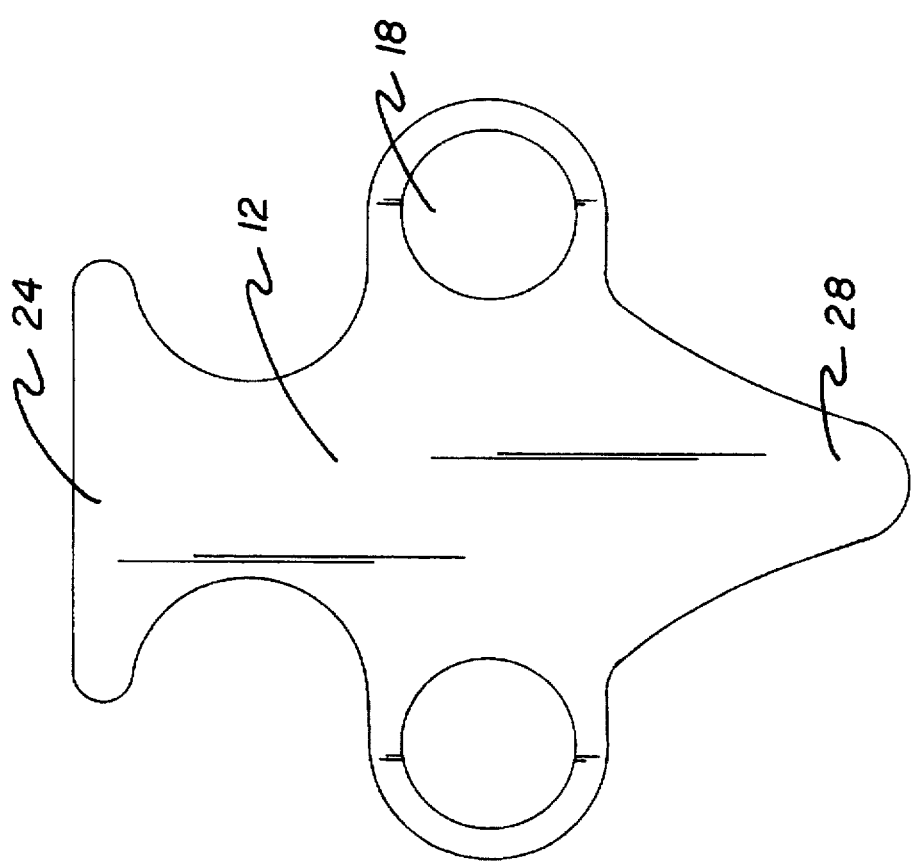
FIG. 5 is a plan view of a second embodiment of the present invention.

A second embodiment of the present invention is shown in FIG. 5 and includes substantially all of the components of the present invention wherein the planar member 12 is adapted for use between two finger's on the hand 100 of the user. The planar member 12 is equipped with one generally T-shaped member 24 and one arcuate member 28.

Figure 6:
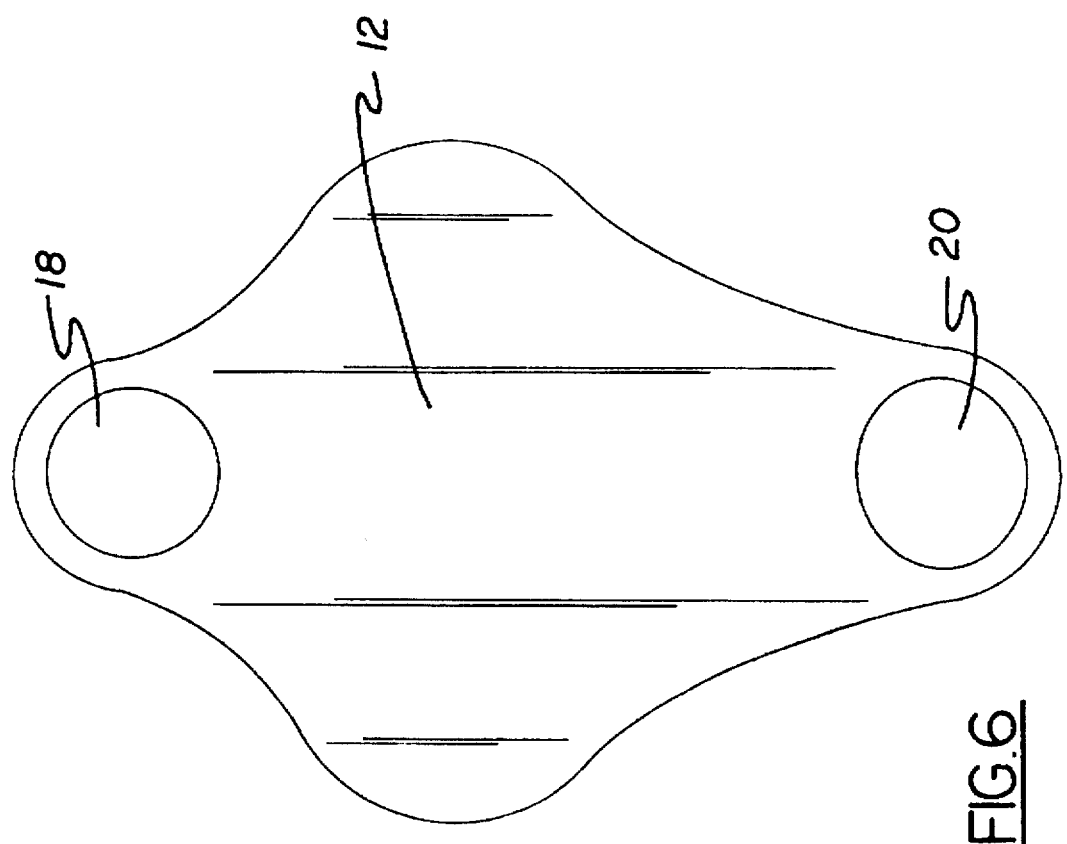
FIG. 6 is a plan view of a third embodiment of the present invention.

A third embodiment of the present invention is shown in FIG. 6 and includes substantially all of the components of the present invention except that the planar member 12 is missing the elongated upper portion 14 with only the lower arcuate portion 16 adapted for positioning between the thumb and index finger on the hand 100 of the user.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A hand support for controlling scar tissue for applying pressure to an individual's hand to preclude excessive scar tissue buildup during healing comprising, in combination:

a planar member comprised of a flexible material having a generally J-shaped main portion, the main portion having an elongated upper portion and a generally arcuate lower portion, the elongated upper portion having four spaced apart digit apertures therethrough, the lower portion having a single digit aperture therethrough, the single digit aperture of the lower portion having a diameter greater than a diameter of the four digit apertures of the elongated upper portion, the planar member being dimensioned to be worn on a hand of a user;

three generally T-shaped members each having lower ends integral with a first edge of the elongated upper portion of the planar member;

three arcuate members each having lower ends integral with a second edge of the elongated upper portion of the planar member.

2. A hand support for controlling scar tissue comprising:

a planar member comprised of a flexible material, the planar member having a plurality of digit apertures therethrough, the planar member being dimensioned to be worn on a hand of a user;

a plurality of generally T-shaped members each having lower ends integral with a first edge of the planar member.

3. The hand support as set forth in claim 2 and further including a plurality of arcuate members each having lower ends integral with a second edge of the planar member.

4. The hand support as set forth in claim 3 wherein the number of generally T-shaped members and arcuate members is one.

5. A hand support for controlling scar tissue comprising:

a planar member comprised of a flexible material, the planar member having a plurality of digit apertures therethrough, the planar member being dimensioned to be worn on a hand of a user, the planar member having a pair of arcuate members each having lower ends integral with opposing edges thereof.

* * * * *